United States Patent [19]

Vig

[11] Patent Number: 5,744,902

[45] Date of Patent: Apr. 28, 1998

[54] CHEMICAL AND BIOLOGICAL SENSOR BASED ON MICRORESONATORS

[75] Inventor: John R. Vig, Colts Neck, N.J.

[73] Assignee: The United States of America as represented by the Secretary of the Army, Washington, D.C.

[21] Appl. No.: 441,909

[22] Filed: May 16, 1995

[51] Int. Cl.$^6$ ................................................ H01L 41/08
[52] U.S. Cl. ................................................ 310/360
[58] Field of Search ................................ 310/309, 320, 310/338, 348, 360, 361, 365, 366

[56] References Cited

U.S. PATENT DOCUMENTS

| | | | |
|---|---|---|---|
| 2,497,275 | 2/1950 | Samuelson | 171/327 |
| 3,339,091 | 8/1967 | Hammond et al. | 310/348 |
| 3,816,773 | 6/1974 | Baldwin et al. | 310/338 |
| 4,109,173 | 8/1978 | O'Connell | 310/313 |
| 4,135,108 | 1/1979 | Besson | 310/344 |
| 4,596,697 | 6/1986 | Ballato | 422/98 |
| 4,754,187 | 6/1988 | Kosinski | 310/361 |
| 4,755,314 | 7/1988 | Sakaguchi et al. | 252/62.9 |
| 4,760,351 | 7/1988 | Newell et al. | 310/320 |
| 4,990,818 | 2/1991 | Ballato et al. | 310/360 |
| 5,015,906 | 5/1991 | Cho et al. | 310/309 |
| 5,043,043 | 8/1991 | Howe et al. | 310/309 |
| 5,151,110 | 9/1992 | Bein et al. | 55/75 |
| 5,187,399 | 2/1993 | Carr et al. | 310/309 |
| 5,189,914 | 3/1993 | White et al. | 73/599 |
| 5,198,716 | 3/1993 | Godshall et al. | 310/349 |
| 5,233,259 | 8/1993 | Krishnaswamy et al. | 310/366 |
| 5,262,127 | 11/1993 | Wise et al. | 422/98 |
| 5,299,868 | 4/1994 | Dennis et al. | 310/361 |
| 5,304,887 | 4/1994 | Heinecke et al. | 310/361 |
| 5,306,644 | 4/1994 | Myerholtz et al. | 436/149 |
| 5,339,051 | 8/1994 | Koehler et al. | 331/65 |
| 5,385,709 | 1/1995 | Wise et al. | 422/98 |

OTHER PUBLICATIONS

McGowan et al, "Chemical/Biological Contaminant Detector for Aqueous Environments: Preliminary Report", 1994 IEEE International Frequency Control Symposium, pp. 401–404, Jan. 1994.

Wohltjen, "Mechanism of Operation and Design Considerations for Vapour Sensors", Sensors & Actuators, (5), pp. 307–325, 1984.

Vig, "High Sensitivity Temperature Sensor and Sensor Array", U.S. Ser. No. 08/397,698, filed Mar. 1, 1995.

Danielsson, "Calorimetric Biosensors", Journal of Biotechnology, 15, pp. 187–200, 1990.

Besson, "A New 'Electrodeless' Resonator Design", Proceedings of the 31st Annual Symposium on Frequency Control, pp. 147–152, 1997.

*Primary Examiner*—Thomas M. Dougherty
*Attorney, Agent, or Firm*—Michael Zelenka; William H. Anderson; George B. Tereschuk

[57] ABSTRACT

A chemical/biological sensor is formed from a coated microresonator array. In operation, both mass changes and temperature changes due to the presence of a particular substance or agent will cause an output frequency change which can be attributed to that particular substance or agent. Further, the frequency changes caused by mass loading can be distinguished from those frequency changes caused by temperature changes due to the heat from adsorption or reaction. This is because frequency changes due to mass loading are independent from frequency changes due to temperature changes, and therefore, by measuring the frequency changes of the microresonators coated with a variety of adsorbers, one can independently separate the two types of frequency changes, and, thereby, identify and quantify the adsorbing agents.

2 Claims, 5 Drawing Sheets

CHEMICAL AND BIOLOGICAL SENSOR BASED ON MICRORESONATORS

GOVERNMENT INTEREST

The invention described herein may be made, used, sold and/or licensed by, or on behalf of, the United States of America without the payment to me of any royalties thereon.

RELATED APPLICATIONS

The present application is related to another pending U.S. Patent application: U.S. application Ser. No. 08/397,698, entitled, "High Sensitivity Temperature Sensor and Sensor Array," filed Mar. 1, 1995, attorney docket number CECOM-5031, which has the same listed inventor.

FIELD OF THE INVENTION

This invention relates to biological/chemical sensors, and particularly to sensors based on calorimetric/gravimetric effects, and more particularly to such sensors which can detect both calorimetric and gravimetric effects to a fraction of a monolayer of a substance.

BACKGROUND OF THE INVENTION

One of the most challenging problems facing today's sensor industry, for both military and commercial applications, is the rapid and accurate detection of chemical and biological agents. This problem is even further complicated by the requirements that the detection technique must be sensitive, accurate, selective, power-efficient and portable.

Heretofore, biological/chemical sensors have been based on either calorimetric or gravimetric effects. For example, surface acoustic wave (SAW) sensors are based on gravimetric effects which produce frequency changes in acoustic devices. Mass deposited on the active surface of the device slows and damps the particle motion in a piezoelectric substrate. Damping of the particle motion causes a reduction in the wave velocity of the acoustic signal which ultimately results in a decrease in the output frequency of the device. These types of sensors have demonstrated that they can detect chemical vapors in air. Such detectors are more fully described in such publications as McGowan et al, "Chemical/Biological Contaminant Detector for Aqueous Environments: Preliminary Report," 1994 *IEEE International Frequency Control Symposium*, pgs. 401–404, January 1994, and Wohltjen, "Mechanism of Operation and Design Considerations for Vapour Sensors," *Sensors & Actuators*, (5), pp. 307–325, 1984.

Also the use of calorimetry for chemical and biological detection has been studied extensively and such detectors have included simple thermistors to bilorimetric sensors based on integrated circuits. A description of the various types of biological and chemical sensors based on calorimetry can be found in "Calorimetric Biosensors," by Danielsson, *Journal of Biotechnology*, 15, pp. 187–200, 1990.

However, to date, no technology has been able to form a sensor which could use both a gravimetric and a calorimetric analysis of chemical/biological agents. The present invention addresses such a new technology.

SUMMARY OF THE INVENTION

Accordingly, one object of the present invention is to provide a sensor which can detect both calorimetric and gravimetric effects caused by the presence of a particular substance or agent.

Another object of the present invention is to provide such a sensor which is sensitive, accurate, selective, power-efficient and portable.

These and other objects of the present invention are accomplished by providing a microresonator array which may have uniform microresonators or varied microresonators and either a coating of a single reactant or a multiplicity of reactants on different microresonators on the array. For the purposes of the present invention, a reactant coating is a coating which acts as a catalyst for, or which adsorbs, absorbs, or reacts with atoms or molecules which come in contact with the coating, or which otherwise contributes to a change in a microresonator's temperature due to the proximity of a chemical or biological agent. The microresonator array which may be used for the present invention is fully described in U.S. application Ser. No. 08/397,698, entitled, "High Sensitivity Temperature Sensor and Sensor Array," filed Mar. 1, 1995, attorney docket number CECOM-5031, which is incorporated herein by reference.

In operation, both mass changes and temperature changes due to the presence of a particular substance or agent will cause an output frequency change which can be attributed to that particular substance or agent. Further, if the array is formed of dual mode resonators the frequency changes caused by mass loading can be distinguished from those frequency changes caused by temperature changes. This is because frequency changes due to mass loading are independent from frequency changes due to temperature changes, and therefore, by measuring the two modes of a dual mode resonator, one can independently separate the two types of frequency changes. This is significant in that a particular calorimetric effect may be the same for more than one reaction. However, if a gravimetric effect can be independently and simultaneously measured for the same occurrence, then high selectivity can be attained for a vast variety of substances or agents.

BRIEF DESCRIPTION OF THE DRAWINGS

These and other features of the invention will become readily apparent in light of the following Detailed Description of the Invention and the attached drawings wherein.

Figure 1A:
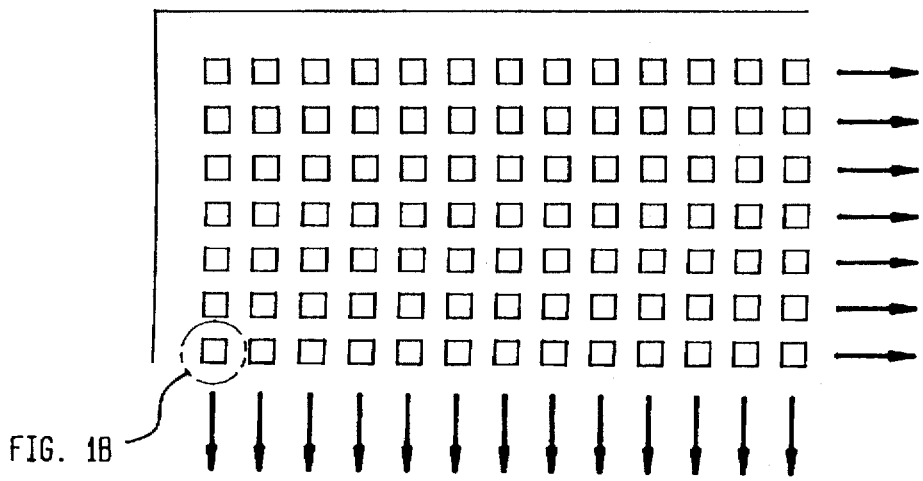
FIGS. 1a and 1b illustrate a top view of a configuration for one electrodeless embodiment of the present invention and the microresonators incorporated into a sample array, wherein the necessary coatings and electrodes are not shown.

It should be noted that for purposes of illustration some of the features of the present invention have not been drawn to scale. However, the examples of preferred dimensions are given in the Detailed Description of the Invention.

DETAILED DESCRIPTION OF THE INVENTION

In its most generic scope the present invention includes a microresonator array which has either a coating of a single reactant or a multiplicity of reactants on different microresonators on the array. The microresonator array according to the present invention is described as follows.

MICRORESONATOR ARRAY

The microresonator according to the present invention may be a single or dual mode crystal, but the crystal must be cut and excited such that it has a steep and monotonic frequency versus temperature characteristic and has a well behaved temperature sensitive mode. As mentioned above, this characteristic for purposes of this invention will be referred to as a thermometer cut crystal.

The types of quartz crystal cuts which may be used for the present invention include the Y-cut, AC-cut, BC-cut, LC-cut, NLSC-cut, SC-cut, or any other cut that can be manufactured to be very thin and have a well behaved temperature sensitive mode. Further, an SC-cut's b-mode, or the beat frequency derived from its fundamental mode and third overtone frequencies can be used as temperature sensing frequencies. The above-mentioned cuts typically have frequency vs. temperature slopes of 20 ppm/°K to 90 ppm/°K (that is, 32 kHz/°K to 140 kHz/°K at 1.6 GHz). For example, a Y-cut or an AC-cut can provide a single mode with a steep frequency versus temperature characteristic; an AC-cut has a slope of +20 ppm/°C. and a Y-cut crystal has a slope of +90 ppm/°C. For a dual mode SC-cut resonator, a typical slope of the beat frequency versus temperature is 80 ppm/°C., but this slope can be varied over a wide range by varying design parameters, such as the electrode dimensions. A slope as high as 150 ppm/°C. has been achieved. Therefore, because the frequency versus temperature characteristics of different cuts vary greatly, the type of cut used for particular applications will greatly depend upon the sensitivity required and the ease of design and fabrication.

As those skilled in the art will also recognize, the microresonators according to the present invention can be made of piezoelectric or dielectric materials other than quartz. For example, langasite, lithium tetraborate, berlinite, lithium niobate, lithium tantalate, zinc oxide, gallium phosphate, gallium arsenide, aluminum nitride, ceramics, silicon, etc, may all be used. Sapphire resonators can provide higher Q and lower noise than quartz resonators of the same frequency.

With respect to the dimensions of the resonator, the diameter to thickness ratios of the various cuts are important. It is also important that when the resonators are plano-plano, the two major surfaces of the resonator be parallel. For example, while a flat AT-cut requires a diameter to thickness ratio of about 80, an SC-cut as well as other cuts only require a ratio of about 30 to 50. A specific example of a resonator which may be used in the present invention would be a 1.6 GHz SC-cut or AC-cut resonator having a thickness of 1 µm. Using such a resonator, a 40,000/cm² "pixel" array can be formed on a single quartz wafer while still maintaining a diameter to thickness ratio of 50. In such an array, each "pixel" would have dimensions equal to 50 µm×50 µm×1 µm. As those skilled in the art will recognize, 10 cm×10 cm wafers are currently available and accordingly, arrays of up to 2,000×2,000, or 4 million pixels, would be possible, in principle. Moreover, using higher frequency resonators, larger numbers of pixels would also be possible. For example, at 3.2 GHz, 4 times as many resonators could be accommodated on the same area.

Because the resonators used for purposes of this invention are small, it will be most advantageous to form the resonators using photolithographic techniques, such as those used in the microelectronics industry. Using such techniques, then, the resonators may take on a variety of shapes including circular, elliptical, rectangular, hexagonal, etc. In addition to using etching processes, epitaxial or other thin film growth techniques may also be employed followed by etching away some or all of the substrate in order to form an array of thin film microresonators.

Now considering the sensitivity of the present invention, the steady-state calorimetric response of any thermal detector may be given by the following equation:

$$\Delta T = \frac{P}{G}$$

where P is the absorbed power resulting from the interaction between the chemical or biological agent and the reactant coating, $\Delta T$ is the temperature rise due to P, and G is the thermal conductance between the sensitive element (i.e., the microresonator) and a heat sink at temperature T. The degree to which the $\Delta T$ can be resolved depends on the noise of the detector element relative to the signal produced by $\Delta T$. The use of low-noise microresonators and low-noise circuitry is, therefore, advantageous.

The time constant $\tau$ of the detector element is given by the equation:

$$\tau = \frac{C}{G}$$

where C is the heat capacity of the element. Therefore, for best performance, the element for any thermal detector should have a small G and a small C/G ratio.

Considering these qualities for the present invention, it is known that the heat capacity of quartz ranges from $111\times10^{-3}$ cal/g at $-100°$ C. to $204\times10^{-3}$ cal/g at $+200°$ C., and $270\times10^{-3}$ cal/g at $+400°$ C. and the thermal conductivity of quartz ranges from 0.117 cal/cm/s/°C. parallel to the Z axis and 0.0586 cal/cm/s/°C. perpendicular to the Z axis, at $-190°$ C., to 0.0215 and 0.0133 at $+100°$ C. (1 cal/sec=4.184 watt–sec=4.184 joules). Therefore, at a temperature of 300° K and using the 1.6 GHz SC-cut dual mode microresonator mentioned above, the increase in radiant heat loss due to a temperature rise is $7.84\times10^{-8}$ watt/°K and the thermal time constant for the radiant heat loss is 0.17 second.

In order to achieve the highest detectivity, the microresonators according to the present invention should be thermally isolated to make the thermal conductance through the supports negligible. This means that the microresonators should be in a low pressure environment. In order to reduce the microresonator's thermal time constant, it is necessary to reduce C/G. For example, this may be accomplished by allowing a small amount of thermal conductance through the supports, or through regulating the pressure and flow of the fluid surrounding the microresonators.

In order to achieve the highest signal to noise ratio with the shortest measurement time capability, a measurement time $\tau$ should be selected at the "knee" of the two-sample deviation $\sigma_y(\tau)$ VS. $\tau$ curve and should be averaged over multiple measurements. The "knee" of the $\sigma_y(\tau)$ vs. $\tau$ curve is the lower end of the "flicker floor," i.e. it is the point where the curve turns up and the white phase noise takes over from flicker of the frequency region.

As mentioned above, a dual-mode, SC-cut resonator has a typical beat frequency vs. temperature slope of 80 ppm/°C., which, for example, equates to 14 Hz/°C. at a 172 kHz beat frequency when the resonator is at 10 MHz in the third overtone and at 3.3 Mhz in the fundamental mode. At a constant temperature, the resolution of the beat frequency measurement is limited by the resonator's short term stability or noise, $\sigma_y(\tau)$. The minimum short term stability, $\sigma_y(\tau)$, of a 1.6 Ghz bulk acoustic wave (BAW) resonator has been estimated to be approximately $10^{-10}$ to $10^{-9}$. If a measurement time for the present invention is set at the "knee" of the $\sigma_y(\tau)$ vs. $\tau$ curve, the measurement time $\tau$ would be at approximately $10^{-4}$s. Using this measurement time and assuming the micro-resonators remain stable as a function of environment for 1 second, 10,000 measurements can be made at $\tau=100$ μs. Therefore, in a scanning configuration, if switching to the next pixel and measuring the frequency is done, for example every 100 μs, one oscillator can excite 10,000 resonators per second. The methods of excitation include exciting all resonators simultaneously, with one oscillator per microresonator, or exciting resonators by scanning, that is, with one oscillator exciting a multiplicity of microresonators sequentially. When the array consists of a large number of pixels, or when power availability is limited, the scanning method is preferred. A large array can, for example, be divided into subarrays with one oscillator exciting the microresonators in each subarray.

Of course, as those skilled in the art will readily recognize, 1.6 GHz resonator arrays as described above are difficult to fabricate with currently available materials and fabrication methods. Until better materials and fabrication methods become available, thicker microresonators, for example, 500 MHz microresonators may also be used according to the present invention and will make the present invention much easier to fabricate as well as reduce the noise. Microresonators of up to 30 μm in thickness may be utilized in the present invention. Compared with the 1.6 GHz example, the pixels for a 500 MHz embodiment would be about three times thicker and nine times greater in area. For example, at 500 MHz, a pixel's dimensions will be 150 μm×150 μm×3 μm and therefore, 4,400 pixels per $cm^2$ are possible. Using the calculations above, the thermal resolution of the a 500 MHz array would be approximately 100 nanokelvins. Although 500 MHz and even lower frequency microresonators are adequate for many applications, the performance capability of the microresonators improve when the frequencies are higher, e.g., 3.2 GHz microresonators will eventually be preferred to 1.6 GHz, once 3.2 GHz microresonators become manufacturable. At 3.2 GHz, for example, the thickness of an SC-cut microresonator is about 0.5 μm.

Figure 1B:
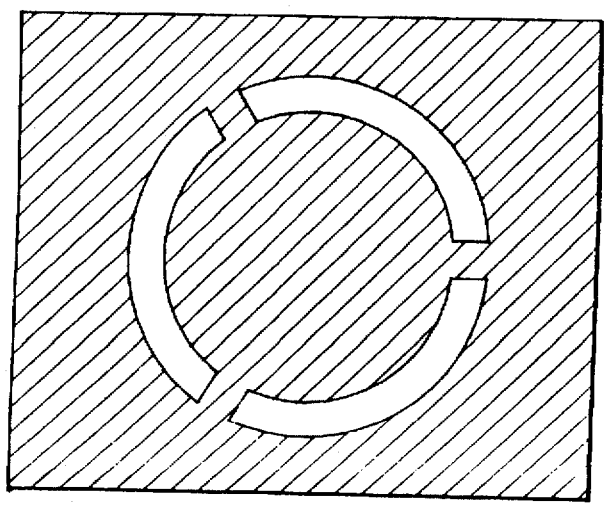

Referring now to FIG. 1b, there is shown one electrode configuration for the microresonator according to the present invention. FIG. 1b shows a configuration for a thickness field resonator with a ring or solid electrode on the front side of a crystal and a ring or solid electrode on the back side (these electrodes are not shown). Other electrode configurations are also possible.

Figure 2A:
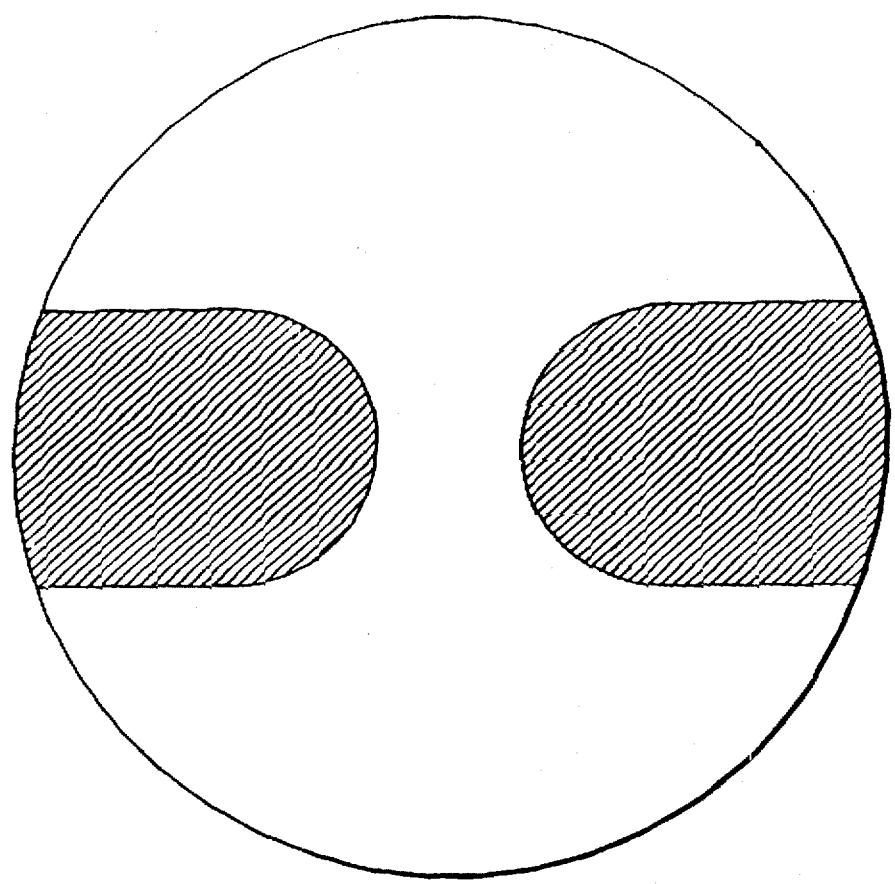
FIGS. 2a and 2b illustrate top and cross-section views of a second electrode configuration, that of a lateral field resonator, according to the present invention, wherein the reactant coating is not shown.
Figure 2B:
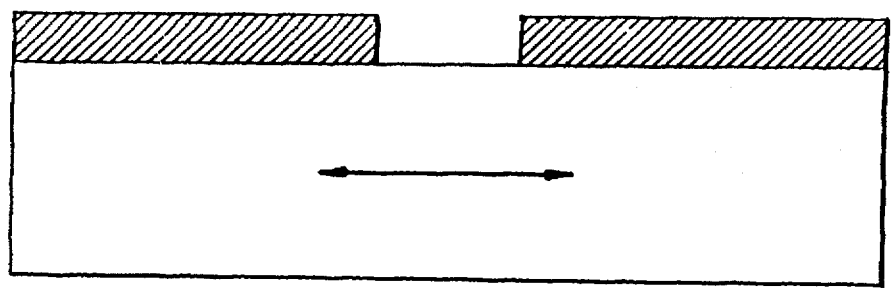

As shown in FIGS. 2a–2b, a lateral field resonator may also be employed in the present invention. FIGS. 2a–2b show that using lateral field excitation, according to one embodiment of the invention, only one side of the crystal needs to have electrodes, leaving the entire surface of the opposite side to be coated with a reactant. Further, a lateral field resonator could be coated on one side with the necessary two electrodes and the other side could be coated with a thin film reactant coating. Furthermore, the resonator's energy trapping can be aided by either recessing the electrodes into the crystal substrate or by creating mesas in the crystal substrate or by using the reactant coating's mass distribution to achieve the energy trapping.

One method of fabricating the resonators is to etch the resonators such that the center portions are slightly thicker than the rest. This mesa formation would provide the necessary energy trapping. An example of dimensions for this would include a diameter for the central mesa to be equal to the diameter of the outer edge of the electrode and the thickness of the mesa would be about one fiftieth of the plate thickness, that is, for a one micrometer thick microresonator, the mesa height would be only about 20 nanometers. Another way to form the mesa is to deposit the reactant coating in the required thickness and shape.

Figure 3:
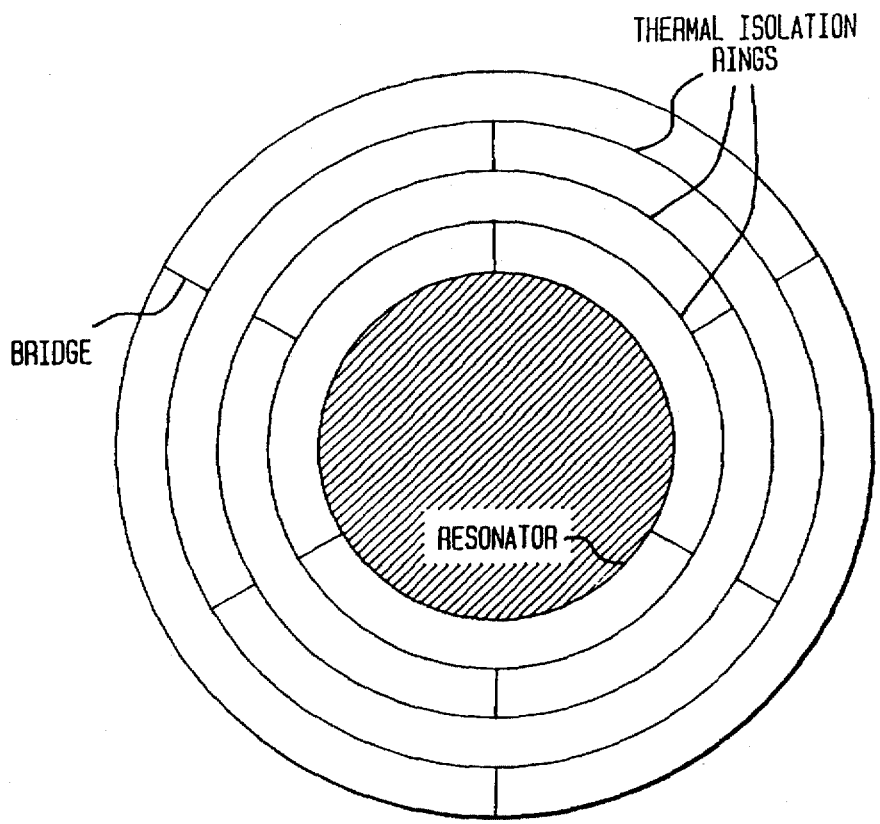
FIG. 3 illustrates one way in which to thermally isolate the microresonator according to the present invention.

Another requirement of the present invention is that the active area of the resonator must be thermally isolated from its support structure. One way to thermally isolate the active areas is shown in FIG. 3, wherein the microresonator includes a plurality of concentric low thermal conductance rings and a plurality of sets of bridges each set of bridges connecting a selected pair of concentric rings. This configuration extends the thermal conduction path length. As shown, concentric rings are etched around each resonator and are connected, for example, by a set of three evenly spaced bridges which are each separated by 120° such that the bridge sets are offset from each other by 60°. With this configuration, the heat conduction must travel through a bridge around two 60° arcs before passing to the next ring. For a resonator diameter D, each 60° arc is $\pi D/6$ long. If the bridges' length=b and the arc length=L, then the path per ring is approximately ⅓(L+b). The thermal conductance is determined by the number of rings and the dimensions of the rings and bridges. For example, if D=50 μm, then L=26.2 μm and therefore, conduction losses may be reduced to below radiation losses if the rings and bridges are 2 μm wide by 0.5 μm thick, b=3 μm and the number of rings=10. In this embodiment, the effective path length for the structure is 120 μm and the thermal conductance is approximately $8\times10^{-8}$ watt/K.

Figure 4:
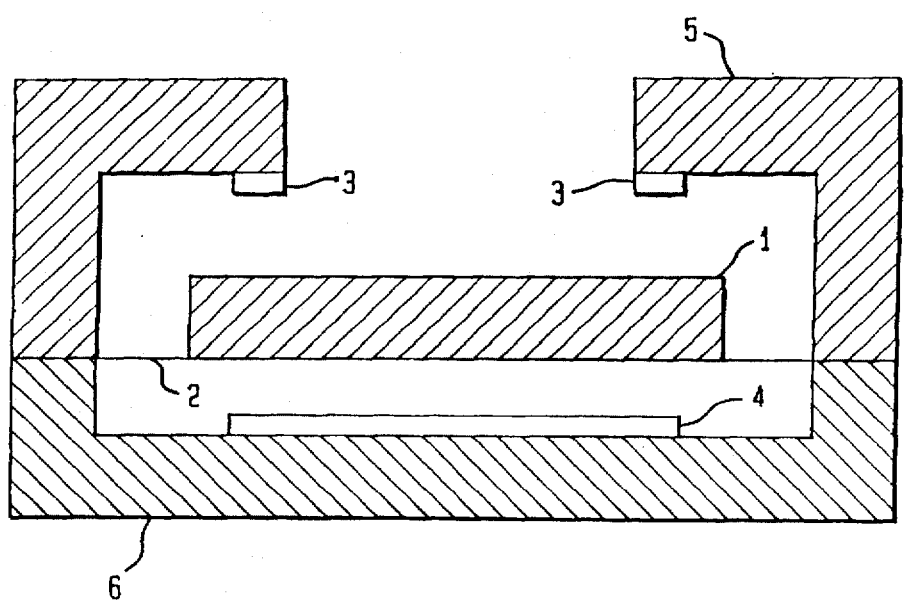
FIG. 4 illustrates another way in which to thermally isolate the microresonator according to the present invention.

Another way to thermally isolate the microresonator would be to support the resonator on thin film supports as shown in FIG. 4. As shown, a resonator wafer 1 is supported by thin film support(s) 2, which itself is supported by sandwiching the thin film supports between electrode wafers 3 and 4. The resonator wafer is excited in an electrodeless or BVA configuration by top electrodes 5 and bottom electrodes 6. Such electrodeless configurations are known in the art and have been described in such references as U.S. Pat. No. 3,339,091 issued to Hammond et al on Aug. 29, 1967 and Besson, "A New Electrodeless' Resonator Design," Proceedings of the 31$^{st}$ Annual Symposium on Frequency Control, pp. 147–152, 1997, both of which are incorporated herein by reference. An advantage of the electrodeless configuration is that direct electrical contacts to the resonator are not needed. Therefore, resonators supported by only mechanical contact are only limited by how thin and narrow the thin film supports can be. This thin film may, for example, be built up of monolayers, either self assembling or Langmuir-Blodgett films, of an infrared absorbing material. Another example of a thin film support is a masked pattern which is attached to one side of the resonator wafer wherein the masked pattern is a thin, low thermal conductance etch resist pattern such that when etching is completed the pattern serves as the mechanical connection to the electrodeless configuration described above. Another means of thermally isolating the microresonator is to use an aerogel support(s).

Figure 5:
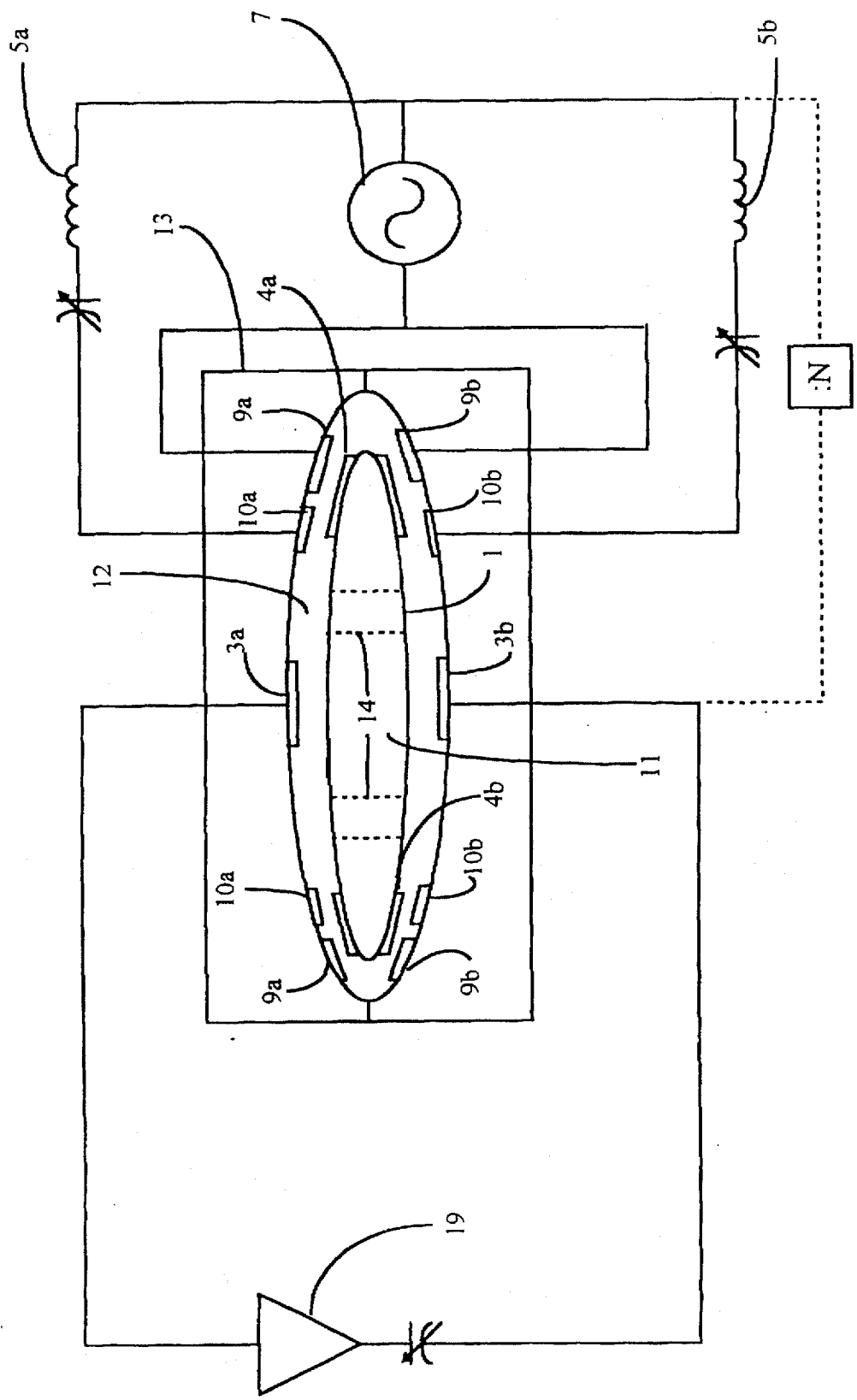
FIG. 5 illustrates still another way in which to thermally isolate the microresonator according to the present invention.

Still another means of thermally isolating the microresonator is to levitate the resonator and excite the resonator in an electrodeless configuration. In FIG. 5, there is shown one preferred embodiment of the present invention. As shown, a BVA style or electrodeless resonator 1 is levitated utilizing two LC resonant circuits as described above, but with ring shaped capacitor elements mounted on the housing and the resonator. The resonator according to the present invention can be any type of resonator used in the art, such as crystals of any cut and orientation of quartz, langasite, lithium tetraborate, lithium tantalate, sapphire, etc, or resonators formed of ceramics or other piezoelectric materials. The preferred shape of the resonator plate is circular and biconvex, however, the shape may also be plano-convex, plano-plano, and rectangular. The levitation may also be used with lateral field and conventional thickness field resonators. The electrical leads to the electrodes then can be very thin conducting wires or ribbons, for example. As shown, the resonator 1 is disposed within a cavity 12 of housing 13. Two ring shaped levitation electrodes 9a and 10a are mounted on a top surface 2 of the cavity 12 and two ring shaped levitation electrodes 9b and 10b are mounted on a bottom surface of the cavity 12. Two more ring shaped levitation electrodes 4a and 4b are mounted on resonator 1 preferably on an area outside the active region 11 of the resonator which may be separated by quartz bridges (as represented by dashed lines 14). The levitation electrodes 9a and b and 10a and b are electrically connected to inductors 5a and 5b, respectively, which are both connected to levitation signal source 7. An alternative method of providing a signal to the levitation circuit is to derive the signal from the oscillator circuit 19, for example, by dividing down the oscillator frequency to the levitation frequency, as indicated by the dashed line and the ":N" block.

The active region 11 of the resonator is vibrated/excited by an oscillator circuit. As shown in FIG. 5, electrodes 3a and 3b are mounted on the top and bottom surfaces of the cavity and are electrically connected to an oscillator circuit 19 (represented by an amplifier and tuning element). The resonator is operated in a manner similar to that explained in U.S. Pat. No. 3,339,091, issued to Hammond et al on Aug. 29, 1965, which is incorporated herein by reference. Of course, as those skilled in the art will readily recognize given this disclosure, any number of BVA type or electrodeless circuit configurations are possible. As shown, however, in order to eliminate any mechanical stresses on the resonator, the ring shaped levitation electrodes should be mounted near an outer, inactive region of the resonator and the inactive region, i.e. an outer edge, may be separated from the active region by a ring shaped "bridge," shown as dashed lines 14. The use of such "bridges" is well known in the art and therefore, need not be explained further.

The ring electrodes 9a and b, 10a and b, and 4a and b form a parallel plate capacitor as described in U.S. Pat. No. 5,015,906, issued to Cho et al on May 14, 1991, which is incorporated herein by reference. Together with the inductors 5a and b and oscillator 7 a LC resonant circuit is formed. Therefore, in operation, the resonator is levitated by applying a voltage to the ring shaped electrodes 9a and b at a frequency greater than the natural frequency of the resonant circuit as described in Cho et al. With the two sets of plate capacitors and inductors, six degrees of stability is achieved.

Once the resonator is levitated, the resonator is vibrated/excited by oscillator circuit 19.

Considering now the dimensions of the device, for a capacitor plate area A and a driving voltage V, the vertical levitation force F is proportional to $AV^2d^{-2}$, where d is the distance between the plate and the electrodes that are mounted to the housing. Accordingly, a typical 10 MHz $3^{rd}$ overtone SC-cut resonator may be levitated at a gap of a few micrometers with a voltage of approximately 10 V. In currently used electrodeless (BVA) resonators, the gap between the electrodes and the resonator plate is usually 5 µm and the next generation BVA resonators are expected to use only about 1 µm. Therefore, the BVA gap dimensions are highly compatible with the dimensions needed for levitation at reasonable voltages. Moreover, the frequency of an electrodeless resonator depends only on the sum of two gaps and thus a slight displacement of the resonator in the gaps will not affect the frequency output of the resonator. For example, if two equal gaps of 5 µm are changed to 4 µm gap on one side and 6 µm on the other side, then the sum is the same and the frequency will not be affected. Therefore, displacements in the gap due to shock and vibration do not affect the oscillator frequency as long as the displacement is not so large as to cause the resonator plate to bump against a wall of the enclosure. In order to protect the resonator against such possible bumps, and also during periods when the levitation circuitry is off, one may protect the resonator by placing small bumpers on the walls of the enclosure such that the resonator plate can touch these bumpers only outside the active region 11. The bumpers may be, for example, micromechanical springs or dimples.

The present invention can be operated at any temperature up to just below the phase transition of the resonator material (or up to just below the melting point for materials without phase transitions). For example, when the resonator material is single crystal quartz, the sensor or sensor array can operate from cryogenic temperatures to near 573° C., the phase transition of quartz. When the resonator material is langasite, the sensor or sensor array can operate from cryogenic temperatures to above 1000° C.

SENSOR

Figure 6:
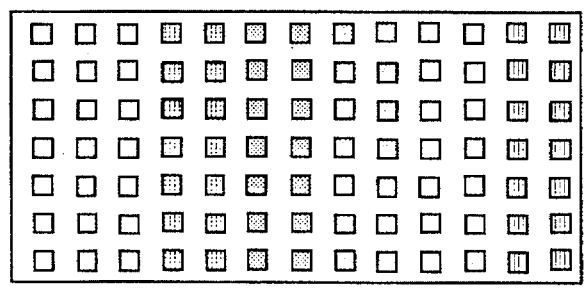
FIG. 6 is an illustration of an array according to FIG. 1 which is partially coated with a reagent according to one embodiment of the invention.

As shown by the varied shading of the different squares which represent independent microresonators. in FIG. 6, microresonators in the array are coated with thin film reactants. The reactants can vary from microresonator to microresonator. Each of the microresonators can be coated with a different reacting film, or, for improved accuracy of measurement and improved certainty of identification, two or more microresonators may be coated with the same reacting film. For example, a 20×20 array can be divided into four 10×10 subarrays, and within each of the subarrays, the 100 microresonators can be coated with the same set of 100 different reacting films.

For a biosensor application, for example, some of the microresonators are coated with one or a plurality of antibodies, and other resonators are not coated at all. With this configuration, the frequency changes caused by a simple mass change due to a contaminant can be distinguished from those caused by an antigen. When an antigen deposits onto an antibody, not only will the frequency change due to the gravimetric effect, but the frequency will also change by a specific amount due to the energy released by the antigen-antibody reaction. similarly, when microresonators are coated with enzymes, the resulting reactions will be exothermic and enthalpy changes in the range of 20–100 kJ/mol (5–25 kcal/mol) will occur. These enzymatic reactions will have a particular "signature", that is a given type of enzyme normally accelerates only one particular type of reaction. The enzymes themselves are normally not affected by the reactions they accelerate. They are normally merely catalysts for specific reactions. Therefore, only small amounts of enzymes, which can be used over and over, can catalyze large quantities of reacting molecules.

A microresonator array, in which the individual resonators are coated with different enzymes, can be used to identify a large variety of chemicals which occur in living organism, as well as other similar chemicals, such as poisons. By using a variety of receptors, each on a different microresonator, an artificial receptor array may be formed for detecting a large variety of biological agents. Given this disclosure though, those skilled in the art will be readily able to realize any number of coatings for the sensor according to the present invention. Therefore, the details with respect to the various coatings for the present invention need not be explained further.

Similarly, for chemical sensor applications, the microresonators of the microresonator array can be coated with a variety of reactants, each chemical reacted would cause a different set of frequency changes. Therefore, from the pattern of frequency changes, any number of chemicals could be identified for any particular calibration of the device.

The microresonators in the array can also be coated with both types of reactants, i.e. chemical and biological. Such an embodiment is both a chemical and a biological sensor.

As was shown above, the amount of energy needed to heat, for example, an array of 1.6 GHz microresonators, by 1° C. is $5 \times 10^{-7}$ cal/cm$^2$ per microkelvin. Typical adsorption and chemisorption energies are in the range of 10 to 100 kcal/mol which is equal to $10^4$ to $10^5$ cal/mol. Assuming surface coverage of $10^{13}$/cm$^2$ which is approximately $10^{-11}$ mol/cm$^2$, then the amount of energy released by the chemical or biological agent is approximately $10^{-7}$ to $10^{-6}$ cal/cm$^2$. This is well within the range of the microresonator array and therefore, a microresonator array according to the present invention could detect the heat produced by a fraction of a monolayer. For example, for 1 GHz microresonators, the frequency noise limitation of the temperature sensitivity is one microkelvin. If one assumes that a molecular layer of an agent consists of $10^{13}$ molecules, then for agents with a heat of adsorption of 25 Kcal/mole, the detectibility limit is about one ten-thousandth ($10^{-4}$) of a molecular layer. Similarly, if one assumes that the reacting molecule's mass is equal to the mass of a quartz molecule (SiO$_2$), then the mass change detectibility limit due to frequency noise is about $3 \times 10^{-5}$ molecular layers. These detectibility limits become smaller as the microresonator frequency increases.

Additional information on the agent, for example, its density-viscosity product, can be obtained by measuring the resonator's admittance. Upon adsorption of, for example, a liquid, not only is the frequency lowered, but the resonance broadens. Therefore, from the reactant induced change in admittance, the density-viscosity product can be calculated.

In another preferred embodiment of the present invention, SC-cut dual mode resonators are formed into an array. The SC-cut dual mode resonators allow one to distinguish between a frequency change caused by mass loading from a frequency change caused by a temperature change. Because the frequency change due to the mass loading is independent from the frequency change due to a temperature change, the two types of frequency changes can be separated by measuring the modes of the dual mode microresonator.

In a single mode embodiment, two microresonators are used, one which is covered with a reagent and one which is not covered with a reagent. In operation, the frequency output of the microresonator which is not covered with a reagent will only reflect a change in pressure and the frequency output of the reagent covered microresonator will reflect a change in both pressure and temperature. Therefore, frequency changes due to temperature changes can be compared against frequency changes due to pressure changes.

The chemical and biological agents to be detected can be introduced into (and removed from) the sensor by means of established techniques, for example, by means of microelectro-mechanical pumps.

In many situations, the reactant coatings on the microresonator will eventually become saturated. In such situations, it is highly desirable to be able to regenerate the reactant coatings. One means of disrobing an adsorbent used as the reactant coating is to heat the microresonators, for example, by irradiating them with infrared radiation from an external IR source. Another means of regeneration is to use ultraviolet-ozone cleaning, as described in U.S. Pat. No. 5,042,288, which is incorporated herein by reference.

Figure 7:
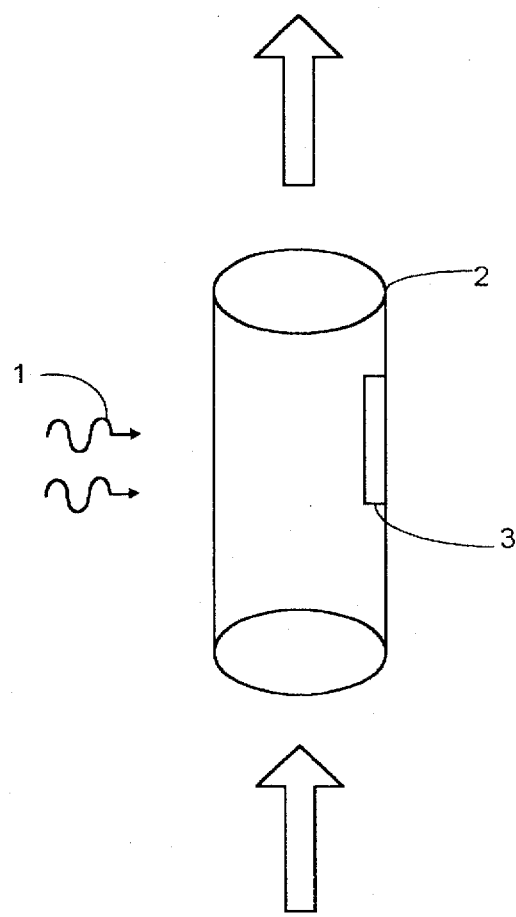
FIG. 7 is an illustration of a gas analyzer according to the present invention.

The present invention could also be incorporated into a gas analyzer. As shown in FIG. 7, a gas analyzer according to the present invention includes a light source 1, a gas chamber or flow tube 2, and a microresonator array 3 described above. The light source 1 emits either a continuum of wavelengths or a spectrum of specific spectral lines of known intensities. The gas present in the chamber or flow tube 2 will absorb specific wavelengths of the light. The microresonator array is configured to detect the various wavelengths or preselected intensities of light and therefore, any wavelength(s) absorbed by the gas present in the chamber or flow tube will be detected. From the known absorbed wavelengths, the gas can then be identified. In one embodiment, a microresonator array and an array of miniature solid-state light emitters, each of which emits a different wavelength, are combined as described above to make a small, highly sensitive gas analyzer. Although FIG. 7 shows a conventional, cylindrical flow tube, a planar arrangement is preferred as that is more compatible with microresonator fabrication. In such an arrangement, the microresonator array is in one plane, and a window, or multiplicity of windows which transmit the wavelengths emitted by the light sources is in another plane. The two planes are separated by a gap through which the gas to be analyzed flows.

What is claimed is:

1. A material sensor comprising:

a dual mode microresonator having an orientation and cut such that the microresonator has a frequency versus temperature characteristic which has a steep slope and is monotonic;

means to electrically excite the microresonator to produce an output frequency such that changes in absorbed energy vary the output frequency;

a reactant coating on the microresonator; and means to thermally isolate the microresonator wherein the means to thermally isolate the microresonator includes a plurality of concentric low thermal conductance rings which are disposed around the microresonator and a plurality of sets of bridges each set of bridges connecting and supporting a selected pair of concentric rings.

2. The sensor of claim 1 wherein each set of bridges includes three bridges which are spaced apart by approximately 120°.

* * * * *